(12) United States Patent
Buchwald et al.

(10) Patent No.: US 9,534,951 B2
(45) Date of Patent: Jan. 3, 2017

(54) MEASURING MODULE FOR REMISSION PHOTOMETRIC ANALYSIS AND METHOD FOR THE PRODUCTION THEREOF

(71) Applicants: JENOPTIK Polymer Systems GmbH, Triptis (DE); Roche Diagnostics Operations, Inc., Indianapolis, IN (US)

(72) Inventors: Jan Buchwald, Jena (DE); Susanne Gaumitz, Weida (DE); Stefan Kalveram, Viernheim (DE); Sebastian Trick, Mannheim (DE)

(73) Assignees: Jenoptik Polymer Systems GmbH, Triptis (DE); Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/426,590

(22) PCT Filed: Sep. 5, 2013

(86) PCT No.: PCT/EP2013/002667
§ 371 (c)(1),
(2) Date: Mar. 6, 2015

(87) PCT Pub. No.: WO2014/037112
PCT Pub. Date: Mar. 13, 2014

(65) Prior Publication Data
US 2015/0241268 A1    Aug. 27, 2015

(30) Foreign Application Priority Data
Sep. 6, 2012   (DE) .................. 10 2012 018 015

(51) Int. Cl.
*H01L 25/16*   (2006.01)
*G01J 1/04*   (2006.01)
(Continued)

(52) U.S. Cl.
CPC .............. *G01J 1/0411* (2013.01); *C23C 14/22* (2013.01); *C23C 14/221* (2013.01); *G01J 1/42* (2013.01);
(Continued)

(58) Field of Classification Search
CPC .................................. G01J 1/0411; G01J 1/42
See application file for complete search history.

(56) References Cited

U.S. PATENT DOCUMENTS 5,260,584 A    11/1993  Popson et al.
6,178,255 B1 *  1/2001  Scott .................. G06K 9/00026
                                                356/71
(Continued)

FOREIGN PATENT DOCUMENTS

DE         198 35 094 A1    2/2000
DE    10 2010 018 052 A1   10/2011
(Continued)

*Primary Examiner* — Tony Ko
(74) *Attorney, Agent, or Firm* — Muncy, Geissler, Olds & Lowe, P.C.

(57) ABSTRACT

A measuring module for remission photometric analysis of one or a plurality of specimens is provided with the following features: a transmitter with a transmission channel for transmitting a measuring radiation to location of the specimen; a first focusing device for focusing the measuring radiation on the specimen; a receiver with a receiving channel to receive the radiation reflected by the specimen; a second focusing device made of plastic for focusing the measuring radiation reflected by the specimen onto the receiver, whereby the second focusing device further comprises a filter which is designed to filter a fluorescence radiation from the specimen excited by the measuring radiation.

12 Claims, 2 Drawing Sheets

(51) Int. Cl.
  *G01N 21/47* (2006.01)
  *G02B 5/20* (2006.01)
  *H01L 31/167* (2006.01)
  *C23C 14/22* (2006.01)
  *G01J 1/42* (2006.01)

(52) U.S. Cl.
  CPC ............... *G01N 21/474* (2013.01); *G02B 5/20* (2013.01); *H01L 31/167* (2013.01); *G01N 2201/0633* (2013.01); *H01L 25/167* (2013.01); *H01L 2924/0002* (2013.01)

(56) References Cited

U.S. PATENT DOCUMENTS

| | | |
|---|---|---|
| 6,844,931 B2 | 1/2005 | Ehbets |
| 8,982,466 B2 | 3/2015 | Neuffer |

FOREIGN PATENT DOCUMENTS

| | | |
|---|---|---|
| DE | 10 2010 048 088 A1 | 4/2012 |
| EP | 1 314 972 A1 | 5/2003 |

* cited by examiner

US 9,534,951 B2

MEASURING MODULE FOR REMISSION PHOTOMETRIC ANALYSIS AND METHOD FOR THE PRODUCTION THEREOF

This nonprovisional application is a National Stage of International Application No. PCT/EP2013/002667, which was filed on Sep. 5, 2013, and which claims priority to German Patent Application No. 10 2012 018 015.2, which was filed in Germany on Sep. 6, 2012, and which are both herein incorporated by reference.

BACKGROUND OF THE INVENTION

Field of the Invention

The present invention relates to a measuring module and to a method for producing a measuring module.

Description of the Background Art

Such measuring modules according to the preamble are sufficiently well known from the prior art and are used for example for analyzing biological specimens, such as blood or urine, or environmental specimens on the basis of the measuring principle of remission, that is to say the light diffusely reflected at the specimen. For this purpose it is necessary that a secondary radiation excited in the specimen by the measuring radiation is filtered, so that the measurement is not falsified. Similarly, direct reflection may be used as the measuring principle. According to the prior art, however, these filters are formed as separate components, for example from glass. The processing of such filters made of glass is expensive, and consequently cost-intensive.

SUMMARY OF THE INVENTION

The object of the present invention is therefore to provide an improved measuring module that is in particular of a more compact construction and can consequently be produced at lower cost.

The invention provides a measuring module for the remission photometric or reflection photometric analysis of one or a plurality of specimens, the measuring module having the following features: a transmitting device with a transmitting channel for emitting a measuring radiation to the location of the specimen; a first focusing device for focusing the measuring radiation onto the specimen; a receiving device with a receiving channel for receiving the radiation reflected by the specimen; a second focusing device made of plastic for focusing the measuring radiation reflected by the specimen onto the receiving device, characterized in that the second focusing device also comprises a filter, which is designed for filtering a secondary radiation of the specimen that is excited by the measuring radiation. According to the invention, a secondary radiation is understood as meaning the radiation that may adversely affect the actual measuring signal, such as for example the autofluorescence of the specimen, secondary maxima of the light source or transmitting device, ambient light, etc. The combination of the second focusing device with the filter to form a structural unit makes it possible to dispense with additional components. Moreover, such an arrangement proves to be compact and easy to handle.

According to the invention, a measuring module is understood as meaning a measuring unit that receives and detects by means of a receiving device the radiation 12b from a transmitting device reflected at a specimen to be investigated. According to the invention, a transmitting channel and a receiving channel are understood as meaning any path that carries a measuring radiation from a transmitting device to one or a plurality of specimens and also carries the reflected measuring radiation to a receiving device.

The filter is preferably formed as a filter layer, the layer having to comprise a number of layers, and consequently being formed as a layer system. For example, the layer system may comprise the materials silicon oxide, tantalum pentoxide and/or titanium oxide in alternating sequence. The total filter layer preferably has a thickness of greater than 0.5 µm and less than 4.5 µm. The individual layers of the layer system preferably have a thickness of greater than 10 nm and less than 300 nm. The filter or the filter layer can consequently be understood as an interference filter.

According to the invention, a filter should be understood as meaning any optical unit that selects the incident secondary radiation of a specimen.

Furthermore, the invention also provides a method for producing a measuring module according to the invention, with the following features: producing a first and a second focusing device by means of plastic; encapsulating the first and second focusing devices in such a way that a housing is formed; vapor depositing a filter onto the second focusing device. In a further configuration of the invention, the filter is vapor deposited onto at least one of the two focusing devices 5; 6 (FIG. 2). On both focusing devices it may then be advantageous if, for example, a secondary radiation occurs at the illuminating unit or transmitting unit. FIG. 2 shows such a basic representation with at least two filters 11; 11'. The filter may also be configured in such a way that it is adapted directly to the surface of the focusing device, see 11'.

It is both possible that the first and second focusing devices are produced in a first method step, and the two focusing devices are subsequently encapsulated by means of plastic, so that a housing is formed. Alternatively, it is also possible to change the method steps over in time, and consequently to mold the plastic housing first. Such method sequences are also known to a person skilled in the art as two-component injection-molding processes.

The step of vapor depositing the filter preferably takes place by a PVD vapor-depositing process by means of an ion-beam-assisted plasma source. Such a method is very well suited for depositing thin layers, the layers also having a high degree of purity.

It goes without saying that the embodiments just described can be presented on their own or in combination with one another. Further important features of the present invention emerge from the following detailed description in conjunction with the claims and figures. A preferred exemplary embodiment of a measuring module according to the invention is described below and explained in more detail by means of the figure.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
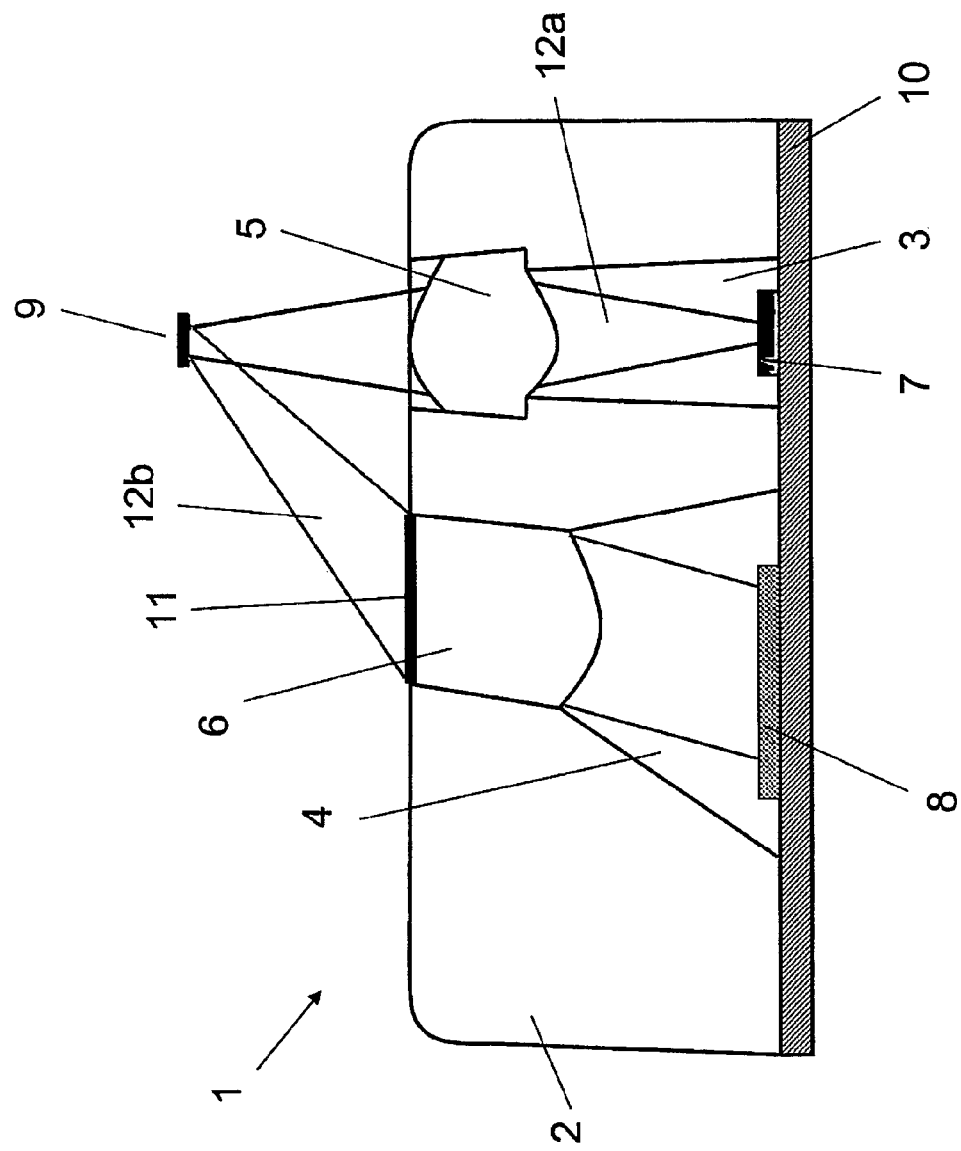
FIG. 1 schematically shows the structure of a measuring module 1 according to the invention. Such a measuring module is suitable for example for measuring and analyzing the radiation reflected at biological or environmental specimens 9.
Figure 2:
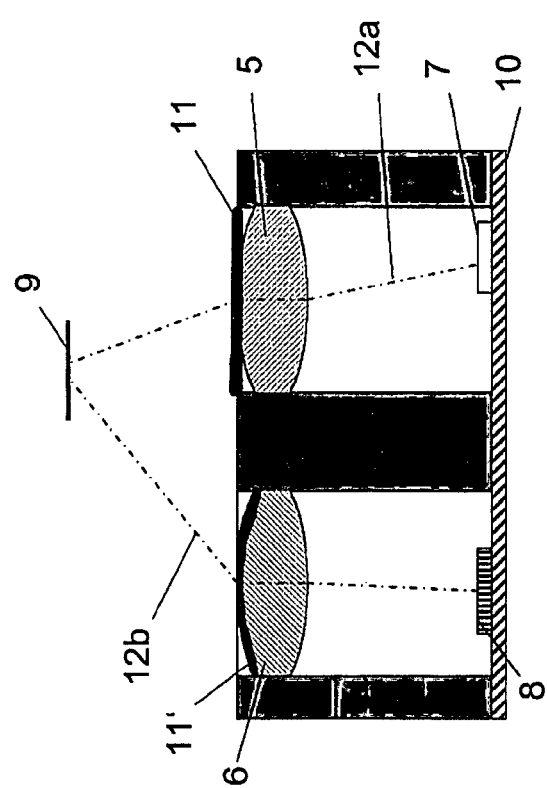
FIG. 2 shows a basic diagram of an optical measuring module according to the present invention in an alternative embodiment.

The measuring module comprises at least one transmitting device 7. The transmitting device is formed as one or a plurality of light-emitting diodes. For example, the one or the plurality of light-emitting diodes radiates a quasi-monochromatic measuring radiation 12a in the range of 300 nm to 1300 nm. In one particular type of embodiment, the measuring radiation has a wavelength of 365 nm. Arranged downstream of the transmitting device, in a transmitting channel 3, is a first focusing device 5, which is formed as focusing beam optics and focuses the measuring radiation onto the specimen 9 to be investigated. The specimen 9 is held for example in a separate specimen holder (not represented), it being possible for the specimen holder to be formed so as to be able to receive a number of specimens. According to the invention, the focusing beam optics are formed as a converging lens made of plastic, preferably produced by the injection-molding process.

The radiation reflected by the specimen 9 (known as remission) is detected by means of a receiving device 8, in order to obtain the corresponding measured values, on the basis of which the composition of the specimen can be concluded. One or a plurality of photodiodes may be used for example as the receiving device 8. The plurality of photodiodes are preferably combined into arrays and connected in parallel or in series, in order to increase the sensitivity of the receiving device and provide a sufficiently large measuring zone.

In order to focus the reflected measuring radiation onto the receiving device 8, arranged upstream of it, in a receiving channel 4, is a second focusing device 6. The second focusing device 6 is likewise formed as focusing beam optics made of plastic.

It is thus provided according to the invention that only the radiation reflected by the specimen should be evaluated. Secondary radiation excited by the measuring radiation should not be accessible to the measurement. In order to exclude this secondary radiation, which may for example have a wavelength shift from the transmitting device of 20 nm to 200 nm, in one particular embodiment 460 nm, from the measurement, the invention provides a filter 11, which is vapour deposited onto the second focusing device. This may be performed for example by a PVD vapor-depositing process (Physical Vapor Deposition).

All of the components of the module are accommodated in one and the same housing 2. The housing 2 may be produced for example by a first injection-molding process, while the optical components, such as the first and second focusing devices, may be produced in a second, subsequent injection-molding process. Such a process is also known to a person skilled in the art by the term "two-component injection-molding process". Here it is possible both that the housing is molded first and, conversely, that the optical components are molded first. The housing is closed off by a baseplate 10, which may likewise be formed from plastic.

For operating the receiving device 8, a control device (not represented) is also provided. This control device interacts with the transmitting device 7 and provides switching signals for it. Furthermore, the control device comprises an amplifier for the radiation measured by the receiving device.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A measuring module for the remission photometric analysis of at least one specimen, the measuring module comprising:
a transmitting device with a transmitting channel emitting a measuring radiation to a location of the specimen;
a first focusing device focusing the measuring radiation onto the specimen;
a receiving device with a receiving channel receiving the radiation reflected by the specimen;
a second focusing device made of plastic focusing the measuring radiation reflected by the specimen onto the receiving device,
wherein the second focusing device also comprises a filter, wherein the filter is formed as a filter layer, wherein the filter layer is formed as a multilayered system and has a thickness greater than 0.5 μm and less than 4.5 μm,
the filter removing a secondary radiation that is excited by the measuring radiation including autofluorescence of the specimen, secondary maxima of the transmitting device, or ambient light.

2. The measuring module as claimed in claim 1, wherein the individual layers of the multilayered system have a thickness of greater than 10 nm and less than 300 nm and comprise the following materials in alternating sequence: silicon oxide, tantalum pentoxide and/or titanium oxide.

3. The measuring module as claimed in claim 1, wherein the transmitting device, the receiving device, the first and second focusing devices are arranged in one and the same housing, in particular made of plastic.

4. The measuring module as claimed in claim 1, wherein the transmitting device is formed as one or a plurality of light-emitting diodes and the receiving device is formed as one or a plurality of photodiodes.

5. The measuring module as claimed in claim 1, wherein the transmitting device and the receiving device are arranged in a first plane.

6. The measuring module as claimed in claim 5, wherein the first focusing device and the second focusing device are arranged in a second plane, wherein the specimen is arranged in a third plane, and wherein the first plane is parallel to the second plane and the third plane.

7. The measuring module as claimed in claim 1, wherein the first focusing device is an aspheric lens.

8. The measuring module as claimed in claim 1, wherein the specimen is disposed in a specimen holder.

9. A method for producing a measuring module as claimed in claim 1, the method comprising:
a) producing the first and second focusing devices by means of plastic;
b) encapsulating the first and second focusing devices in such a way that a housing is formed; and c) vapor depositing a filter onto the second focusing device.

10. The method according to claim 9, wherein steps a) and b) are performed in the reverse sequence, to be precise in such a way that first a housing is produced by means of plastic and then the housing with the first and second focusing devices is encapsulated.

11. The method as claimed in claim 9, wherein method steps a) and b) are performed by the two-component injection-molding process.

12. The method as claimed in claim 9, wherein step c), vapour depositing, is performed by a PVD vapor-depositing process with an ion-beam-assisted plasma source.

* * * * *